(12) United States Patent
Eller et al.

(10) Patent No.: US 9,084,675 B2
(45) Date of Patent: Jul. 21, 2015

(54) VOCAL FOLD MOVEMENT TRANSLATION DEVICE AND METHOD OF USING SAME

(71) Applicants: Derek Roe Eller, Cincinnati, OH (US); Erik M. Meyer, West Chester, OH (US)

(72) Inventors: Derek Roe Eller, Cincinnati, OH (US); Erik M. Meyer, West Chester, OH (US)

(73) Assignee: Cook Medical Technologies LLC, Bloomington, IN (US)

( * ) Notice: Subject to any disclaimer, the term of this patent is extended or adjusted under 35 U.S.C. 154(b) by 382 days.

(21) Appl. No.: 13/737,382

(22) Filed: Jan. 9, 2013

(65) Prior Publication Data

US 2014/0195245 A1 Jul. 10, 2014

(51) Int. Cl.
*A61F 2/20* (2006.01)
*G10L 13/02* (2013.01)

(52) U.S. Cl.
CPC .. *A61F 2/20* (2013.01); *G10L 13/02* (2013.01)

(58) Field of Classification Search
CPC ........................................................ A61F 2/20
USPC .................................................. 607/3; 623/9
See application file for complete search history.

(56) References Cited

U.S. PATENT DOCUMENTS

| 5,111,814 A | 5/1992 | Goldfarb |
| 5,306,298 A | 4/1994 | Godley, III et al. |
| 5,693,096 A | 12/1997 | Bettez et al. |
| 7,917,220 B2 | 3/2011 | Muller et al. |
| 8,065,014 B2 | 11/2011 | Zealear |
| 8,136,532 B2 | 3/2012 | Lindenthaler et al. |
| 2008/0188931 A1 | 8/2008 | Kwon |
| 2009/0099595 A1 | 4/2009 | Cheng et al. |

*Primary Examiner* — Susan McFadden
(74) *Attorney, Agent, or Firm* — Liell & McNeil

(57) ABSTRACT

A vocal fold movement translation device includes a reverse motion linkage configured to interface with a first vocal fold and a second vocal fold. The reverse motion linkage includes a mechanical component configured to move the first vocal fold in a first movement direction in response to movement of the second vocal fold in a second movement direction that is opposite the first movement direction. The reverse motion linkage is movable between a first configuration corresponding to an abducted position of the first and second vocal folds and a second configuration corresponding to an adducted position of the first and second vocal folds.

20 Claims, 4 Drawing Sheets

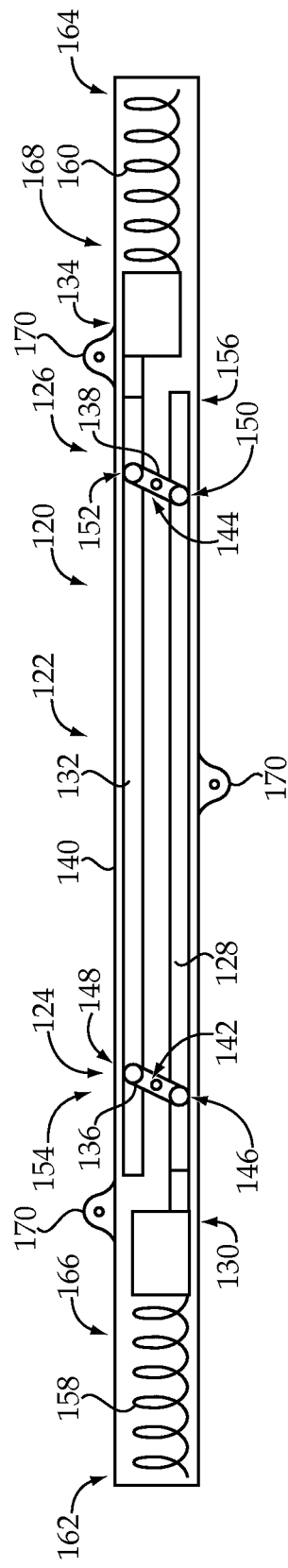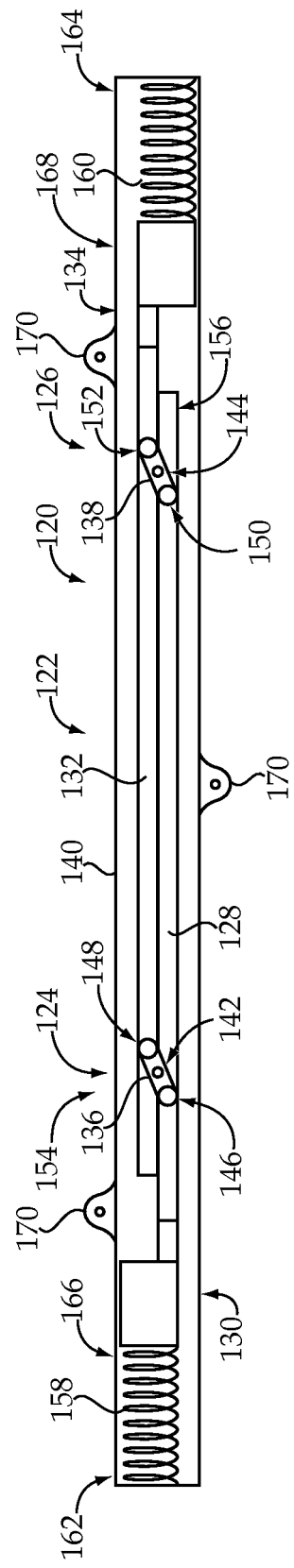
Fig.5
Fig.6

VOCAL FOLD MOVEMENT TRANSLATION DEVICE AND METHOD OF USING SAME

TECHNICAL FIELD

The present disclosure relates generally to a vocal fold movement translation device, and more particularly to a vocal fold movement translation device including a reverse motion linkage for translating movement of a working vocal fold into movement of a non-working vocal fold.

BACKGROUND

Vocal fold paralysis is generally defined as a weakness of one or both of the vocal folds, or an inability of one or both of the vocal folds to move. Vocal fold paralysis may be caused by a number of conditions, including conditions damaging nerves going to the vocal folds. Patients with vocal fold paralysis may be unable to speak clearly or loudly, and may run out of air easily. In addition, since the vocal folds protect the airway and prevent food, drink, and saliva from entering the trachea, vocal fold paralysis may present issues for the patient with regard to swallowing and choking. Most cases of vocal fold paralysis involve unilateral vocal fold paralysis, in which only one of the vocal folds is paralyzed.

Depending on the cause and the extent of the vocal fold paralysis, treatment options may include therapy and/or surgery. For example, if the vocal folds are paralyzed in an adducted, or closed, position, a tracheotomy may be performed to improve breathing. Alternatively, one or both of the vocal folds may be surgically repositioned. With specific reference to unilateral vocal fold paralysis, treatment options may include medialization, which generally refers to the repositioning of the paralyzed, or non-working, vocal fold closer to the non-paralyzed, or working, vocal fold, making it easier for the working vocal fold to move more effectively. Medialization can be accomplished by injecting a substance, or filler, into the non-working vocal fold, or by placing a block of artificial material into the larynx from the outside of the neck.

For example, U.S. Patent Application Publication 2008/0188931 to Kwon teaches an implant inserted into a vocal fold endoscopically to treat unilateral vocal fold paralysis. More particularly, the Kwon reference teaches a cricoid wedge implant that medializes an arytenoid cartilage of a patient. The insertion method for implanting the cricoid wedge implant of Kwon is intended to be less invasive than conventional implant procedures. However, the Kwon implant procedure and other similar procedures for treating unilateral vocal fold paralysis all suffer from similar drawbacks. In particular, by inducing a medialized position of the non-working vocal fold, the airway passage of the patient is always partially blocked, even when the vocal folds are not being used.

The present disclosure is directed toward one or more of the problems or issues set forth above.

SUMMARY OF THE DISCLOSURE

In one aspect, a vocal fold movement translation device includes a reverse motion linkage configured to interface with a first vocal fold and a second vocal fold. The reverse motion linkage includes a mechanical component configured to move the first vocal fold in a first movement direction in response to movement of the second vocal fold in a second movement direction that is opposite the first movement direction. The reverse motion linkage is movable between a first configuration corresponding to an abducted position of the first and second vocal folds and a second configuration corresponding to an adducted position of the first and second vocal folds.

A method of operating a vocal fold movement translation device includes a step of interfacing with a non-working vocal fold and a working vocal fold using a reverse motion linkage of the vocal fold movement translation device. An indication of a movement of the working vocal fold in a first movement direction is received at the reverse motion linkage. The non-working vocal fold is moved in a second movement direction, which is opposite the first movement direction, using a mechanical component of the reverse motion linkage in response to the movement of the working vocal fold.

BRIEF DESCRIPTION OF THE DRAWINGS

FIG. 5 is a front schematic view of another embodiment of a vocal fold movement translation device in a configuration corresponding to an abducted position of the vocal folds, according to the present disclosure;

FIG. 6 is a front schematic view of the vocal fold movement translation device of FIG. 5 in a configuration corresponding to an adducted position of the vocal folds, according to the present disclosure;

DETAILED DESCRIPTION

Figure 1:
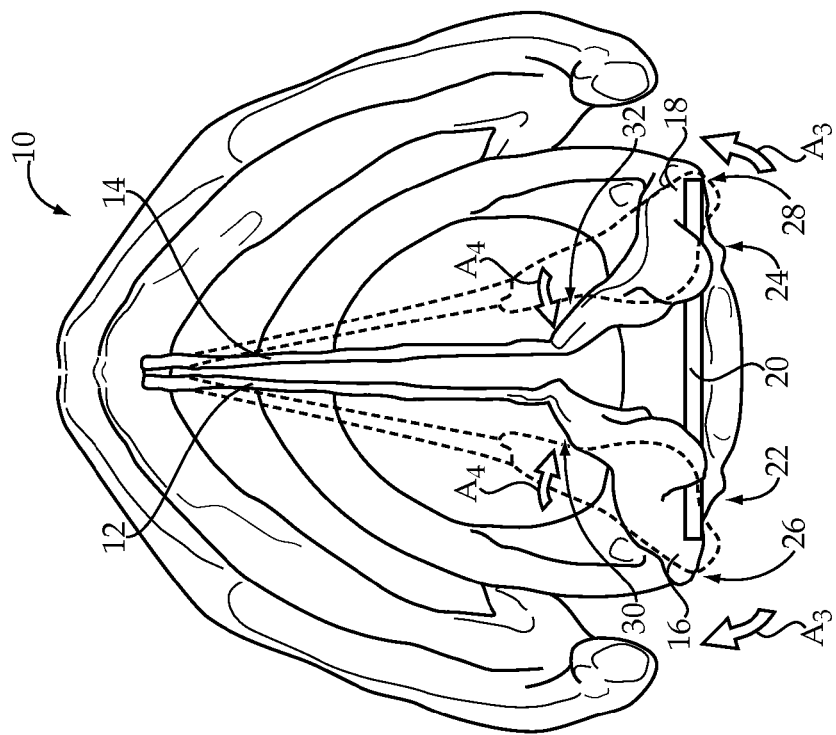
FIG. 1 is a schematic drawing of a larynx, depicting a vocal fold movement translation device facilitating an abducted position of the vocal folds.

Referring to FIG. 1, a portion of a larynx 10 of a patient is shown. The larynx 10 is positioned in the throat of a patient and consists of a number of cartilages and muscles that house and support the vocal folds 12 and 14 in a known manner. The larynx 10 is positioned where the airway and the esophagus separate and, as such, acts as a valve to protect the airway and lungs. In particular, the vocal folds 12 and 14, which are attached to and movable by paired arytenoid cartilages 16 and 18, open to allow breathing and close during swallowing to prevent food from entering into the lungs. The vocal folds 12 and 14 also close, leaving a small space between the vocal folds 12 and 14, to produce sound. More specifically, as air from the lungs is pushed through the small space between the vocal folds 12 and 14, the vocal folds 12 and 14 vibrate to produce sound.

According to the present disclosure, the first vocal fold 12 may be a non-working vocal fold, while the second vocal fold 14 may be a working vocal fold. As used herein, a "non-working" vocal fold may refer to a paralyzed vocal fold or a vocal fold that does not function normally. A "working" vocal fold may refer to a vocal fold that is not paralyzed or a vocal fold that functions at least more effectively than the non-working vocal fold. Thus, according to the exemplary embodiment, the larynx may represent the larynx of a patient experiencing unilateral vocal fold paralysis, or another similar condition. As such, the first vocal fold 12 may be referenced herein as a non-working vocal fold and the second vocal fold 14 may be referenced herein as a working vocal fold.

Figure 2:
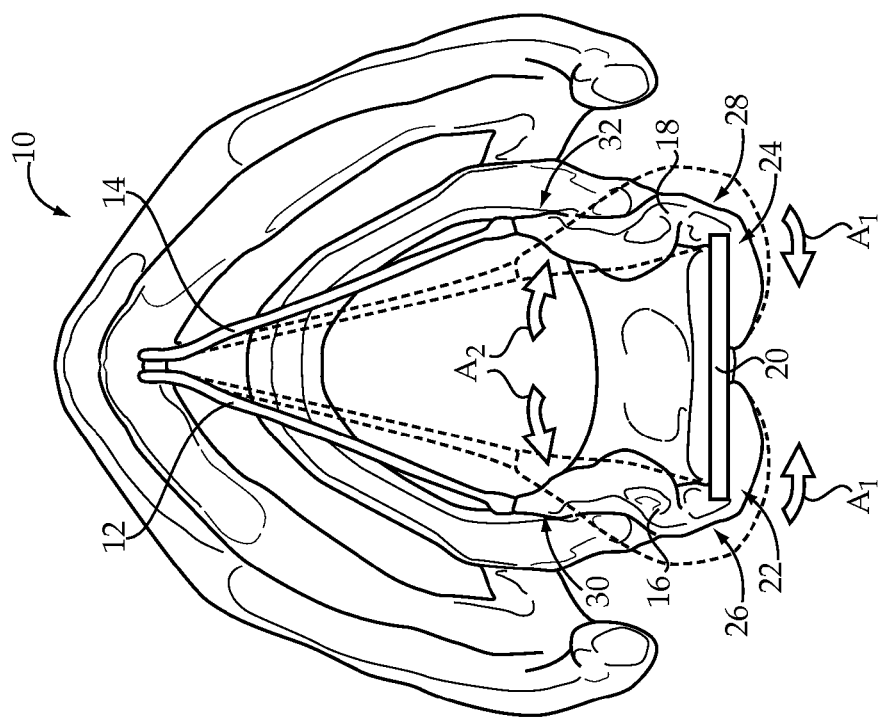
FIG. 2 is a schematic drawing of the larynx of FIG. 1, depicting the vocal fold movement translation device facilitating an adducted position of the vocal folds.

A vocal fold movement translation device 20, as disclosed herein, interfaces with, or interconnects, the non-working vocal fold 12 and the working vocal fold 14. The vocal fold movement translation device 20 is movable between a first configuration, as will be discussed below, corresponding to an abducted position of the vocal folds 12 and 14, as shown in FIG. 1, and a second configuration corresponding to an adducted position of the vocal folds 12 and 14, as shown in FIG. 2. As should be appreciated by those skilled in the art, an "abducted" position refers generally to an open position of the vocal folds 12 and 14, while an "adducted" position refers generally to a closed position of the vocal folds 12 and 14. The vocal fold movement translation device 20, which will be discussed below in greater detail, may have a first end 22 attached to the first arytenoid cartilage 16 supporting the non-working vocal fold 12 and a second end 24 attached to the second arytenoid cartilage 18 supporting the working vocal fold 14. However, alternative attachment locations for facilitating the movement described below are also contemplated.

Movements of the arytenoid cartilages 16 and 18 and, as a result, the vocal folds 12 and 14 are depicted in FIGS. 1 and 2 using arrows. In particular, each of the arytenoid cartilages 16 and 18 may be substantially triangular-shaped, as shown. The first end 22 of the vocal fold movement translation device 20 may be attached toward a first corner 26 of the first arytenoid cartilage 16, and the second end 24 of the vocal fold movement translation device 20 may be attached toward a first corner 28 of the second arytenoid cartilage 18. As shown, the non-working vocal fold 12 may be attached toward a second corner 30 of the first arytenoid cartilage 16, and the working vocal fold 14 may be attached toward a second corner 32 of the second arytenoid cartilage 18. As such, as the first corners 26 and 28 of the arytenoid cartilages 16 and 18 are moved closer together, as shown by arrows $A_1$ in FIG. 1, the second corners 30 and 32 and, thus, vocal folds 12 and 14, are moved away from one another, as shown by arrows $A_2$ in FIG. 1. Movement according to the arrows $A_1$ and $A_2$ repositions the arytenoid cartilages 16 and 18 and the vocal folds 12 and 14 from the positions shown in phantom to the depicted positions. Alternatively, as shown in FIG. 2, if the first corners 26 and 28 of the arytenoid cartilages 16 and 18 are moved away from one another in the direction of arrows $A_3$, the second corners 30 and 32 and, thus, vocal folds 12 and 14, are moved toward one another, as shown by arrows $A_4$. Movement according to the arrows $A_3$ and $A_4$ repositions the arytenoid cartilages 16 and 18 and the vocal folds 12 and 14 from the positions shown in phantom to the depicted positions.

Figure 3:
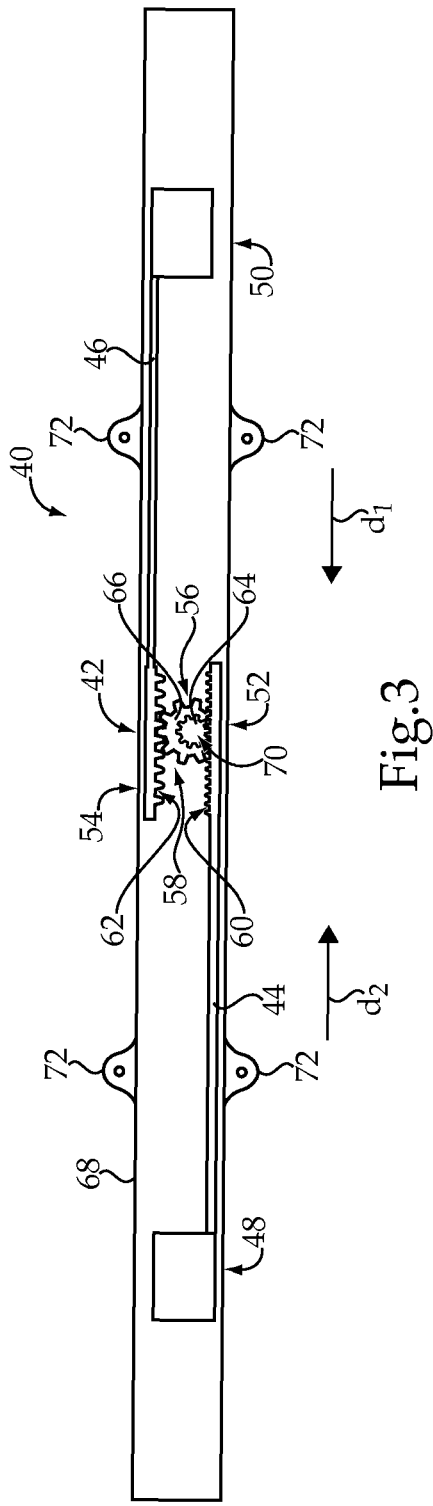
FIG. 3 is a front schematic view of one embodiment of a vocal fold movement translation device, according to the present disclosure.

Turning now to FIG. 3, a first exemplary embodiment of a vocal fold movement translation device 40 is shown. The vocal fold movement translation device 40 may have a position within the larynx 10 similar to the position of vocal fold movement translation device 20 of FIGS. 1 and 2. The vocal fold movement translation device 40 may generally include a reverse motion linkage 42 configured to interface with the vocal folds 12 and 14 of FIGS. 1 and 2. In particular, for example, the reverse motion linkage 42 may include a first lever 44 configured for attachment to the first arytenoid cartilage 16 supporting the non-working vocal fold 12, and a second lever 46 configured for attachment to the second arytenoid cartilage 18 supporting the working vocal fold 14. Although attachment means will be discussed below in greater detail, it should be pointed out that outermost ends 48 and 50 of the first and second levers 44 and 46, which may include enlarged attachment regions, may be attached to the first corners 26 and 28 of a respective one of the arytenoid cartilages 16 and 18, while innermost ends 52 and 54 of the first and second levers 44 and 46 may be interconnected through a single linkage mechanism 56.

The single linkage mechanism 56, according to the embodiment of FIG. 3, may include a rack and pinion mechanism 58. For example, the first lever 44 may include a first toothed rack portion 60 and the second lever 46 may include a second toothed rack portion 62. The first toothed rack portion 60 may be in mesh with a first pinion gear 64 of the rack and pinion mechanism 58, while the second toothed rack portion 62 may be in mesh with a second pinion gear 66 of the rack and pinion mechanism 58. The linkage mechanism 56 may be configured such that, during simultaneous rotation of the first and second pinions gears 64 and 66, a travel distance of the second lever 46 may be greater than a travel distance of the first lever 44. For example, the first pinion gear 64 may be smaller than the second pinion gear 66 and/or may have fewer teeth than the second pinion gear 66.

Since the outermost end 50 of the second lever 46 will be attached to the working vocal fold 14 through the second arytenoid cartilage 18, inward movement of the first corner 28 of the second arytenoid cartilage 18 causes inward movement of the second lever 46. The reverse motion linkage 42, or rack and pinion mechanism 58, translates the inward movement of the second lever 46 into an inward movement of the first lever 44. As should be appreciated, inward movement of the second lever 46 is in a movement direction $d_1$ that is opposite an inward movement direction $d_2$ of the first lever 44. As such, inward movement of the second arytenoid cartilage 18 and, thus, opening of the working vocal fold 14 may translate into a corresponding inward movement of the first arytenoid cartilage 16 and, thus, opening of the non-working vocal fold 12. Similarly, outward movement of the second arytenoids cartilage 18 and, thus, closing of the working focal fold 14 may translate into a corresponding outward movement of the first arytenoid cartilage 16 and, thus, closing of the non-working vocal fold 12.

The first and second pinion gears 64 and 66, which may be configured to rotate together, may be supported on a housing 68 at a common axis of rotation 70 using any known attachment means. The housing 68, according to some embodiments, may be attached to a laryngeal wall, or any other suitable location within the larynx 10. It should be appreciated that the levers 44 and 46 may movably interconnect the artyenoid cartilages 16 and 18 through the single linkage mechanism 56. To provide stability to the vocal fold movement translation device 40, the single linkage mechanism 56 may be secured to the housing 68, which may be secured within the larynx 10 as described above. For example, one or more mounting tabs 72 may be secured within the larynx 10 using sutures or screws. Although not required, the housing 68 may also serve to protect or shield the components of the vocal fold movement translation device 40.

Figure 4:
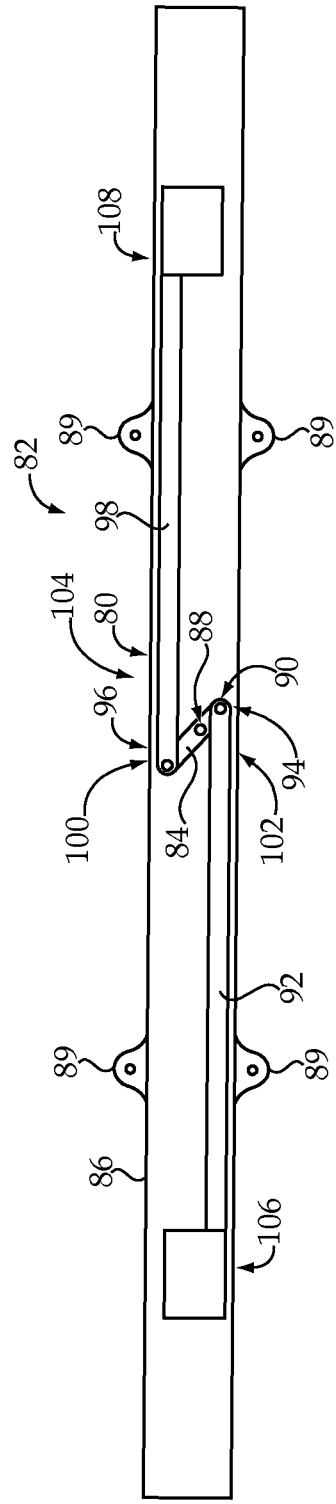
FIG. 4 is a front schematic view of another embodiment of a vocal fold movement translation device, according to the present disclosure.

According to another exemplary embodiment, as shown in FIG. 4, a single linkage mechanism 80 for a vocal fold movement translation device 82 may include a center lever 84 supported on a housing 86. The housing 86 may be attached to a portion of the larynx 10 at a fixed pivot axis 88 or another location along the housing 86. According to some embodiments, the housing 86 may attach to the cricoid cartilage. Mounting tabs 89 may be provided to facilitate attachment of the housing 86. A first end 90 of the center lever 84 may be movably attached to a first lever 92 at a first movable pivot axis 94, while a second end 96 of the center lever 84 may be movably attached to a second lever 98 at a second movable pivot axis 100. The center lever 84 may be attached to innermost ends 102 and 104 of the first and second levers 92 and 98, with outermost ends 106 and 108 of the first and second levers 92 and 98 being configured for attachment to the vocal folds 12 and 14, such as through the arytenoid cartilages 16 and 18, as described above.

Similar to the translated movement described above, the single linkage mechanism 80 of FIG. 4, or an alternative linkage mechanism, may effectively move the non-working vocal fold 12 in a first movement direction in response to movement of the working vocal fold 14 in a second movement direction that is opposite the first movement direction. Further, it may be desirable to reduce the force exerted by the working vocal fold 14 by translating only a portion of the working vocal fold movement. For example, the fixed pivot axis 88 may be closer to the first movable pivot axis 94 than the second movable pivot axis 100. However, as muscles moving the working vocal fold 14 strengthen, it may be desirable to translate all or a majority of the movement of the working vocal fold 14 into movement of the non-working vocal fold 12.

Turning now to FIG. 5, another exemplary embodiment of a vocal fold movement translation device 120 is shown. According to the embodiment of FIG. 5, the vocal fold movement translation device 120 may include a reverse motion linkage 122 having two linkage mechanisms 124 and 126. The reverse motion linkage 122 may include a first lever 128 having an outermost end 130 configured for attachment to the first arytenoid cartilage 16 supporting the non-working vocal fold 12, and a second lever 132 having an outermost end 134 configured for attachment to the second arytenoid cartilage 18 supporting the working vocal fold 14. Each of the two linkage mechanisms 124 and 126 may include a center lever 136, 138 supported on a housing 140 at a fixed pivot axis 142, 144. The first center lever 136 may be movably attached to the first lever 128 at a first movable pivot axis 146 and movably attached to the second lever 132 at a second movable pivot axis 148. The second center lever 138 may be movably attached to the first lever 128 at a third movable pivot axis 150 and movably attached to the second lever 132 at a fourth movable pivot axis 152. As shown, the first linkage mechanism 124 may be positioned toward the outermost end 130 of the first lever 128 and an innermost end 154 of the second lever 132, while the second linkage mechanism 126 may be positioned toward an innermost end 156 of the first lever 128 and the outermost end 134 of the second lever 132.

According to the exemplary embodiment of FIG. 5, the reverse motion linkage 122 may translate all or a majority of the movement of the working vocal fold 14 into a reverse movement of the non-working vocal fold 12. The reverse motion linkage 122 may be movable between a first configuration, as shown in FIG. 5, corresponding to an abducted position of the vocal folds 12 and 14 (FIG. 1), and a second configuration, as shown in FIG. 6, corresponding to an adducted position of the vocal folds 12 and 14 (FIG. 2). To reduce or limit the force exerted by the working vocal fold 14, one or more springs 158 and 160 may be provided to bias the reverse motion linkage 122 toward the first configuration, or abducted position of the vocal folds 12 and 14. According to the illustrated embodiments of FIG. 5 and FIG. 6, the springs 158 and 160 may have outermost ends 162 and 164 attached to the housing 140 and innermost ends 166 and 168 attached to an end of a respective one of the levers 128 and 132. The springs 158 and 160 may have a preload selected to exert the desired biasing force on the levers 128 and 132. One or more mounting tabs 170 may be provided along the housing 140 for securing the vocal fold movement translation device 120 within the larynx 10.

Figure 7:
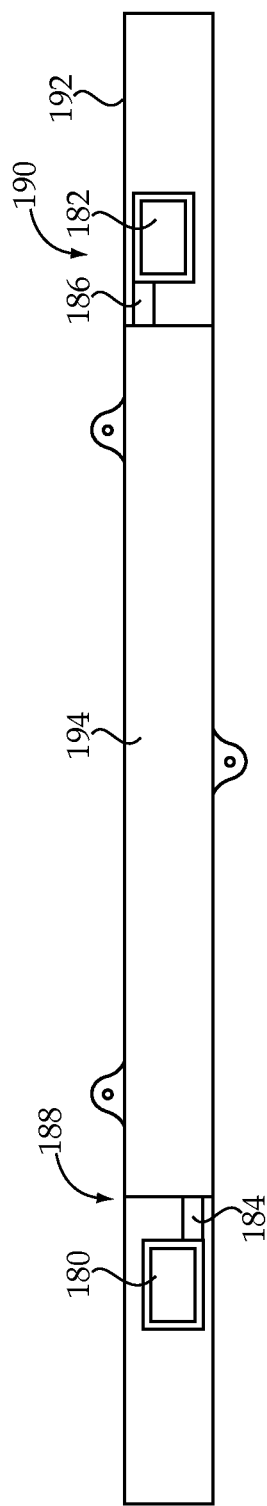
FIG. 7 is a front schematic view of a vocal fold movement translation device, depicting a first means for interconnecting the vocal folds through the vocal fold movement translation device.
Figure 8:
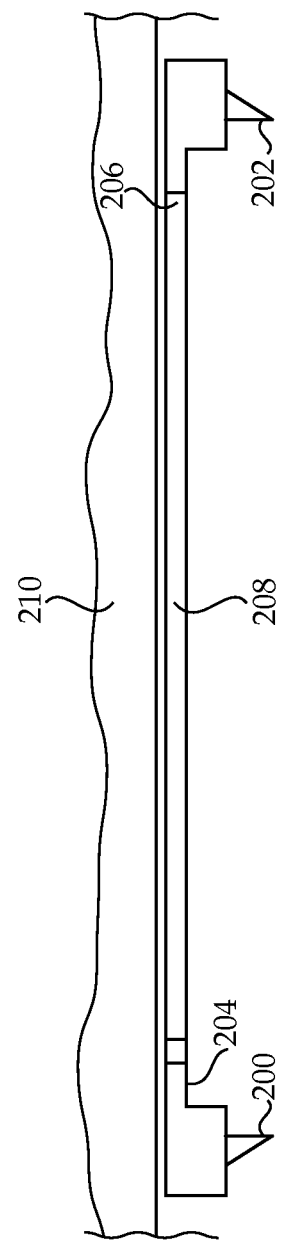
FIG. 8 is a side schematic view of a vocal fold movement translation device, depicting a second means for interconnecting the vocal folds through the vocal fold movement translation device.

Turning now to FIG. 7 and FIG. 8, exemplary attachment means for securing any of the exemplary vocal fold movement translation devices 20, 40, 82, and 120 within the larynx 10 will be discussed. A non-exhaustive list of exemplary attachment means incorporates the use of sutures, bioadhesives, tissue welding, bonding, barbs, or other attachment means. For example, as shown in FIG. 7, bioadhesive layers 180 and 182 may be used for securing levers 184 and 186, which may correspond to one of levers 44, 46, 92, 98, 128, or 132 discussed above, to a respective one of the arytenoid cartilages 16 and 18. In particular, the bioadhesive layers 180 and 182 may be provided at outermost ends 188 and 190 of levers 184 and 186 and may function to secure the outermost ends 188 and 190 to the arytenoid cartilages 16 and 18 in a manner known to those skilled in the art. As is shown, a housing 192, which may be similar to housings 68, 86, and 140 discussed above, may include an additional housing cover 194 for providing additional protection for device components.

According to an alternative attachment means, as shown in FIG. 8, barbs 200 and 202 may be used to attach levers 204 and 206 to a respective one of the arytenoid cartilages 16 and 18 in a known fashion. As is apparent from the side view of FIG. 8, a housing 208 may also be attached to a portion of the larynx 10, such as the laryngeal wall 210, or, for example, the cricoid cartilage, to provide improved stability, as described above. As should be appreciated, similar attachment means to those described with respect to attachment of the levers 204 and 206 to the arytenoid cartilages 16 and 18 may be used for securing the position of the housing 208 within the larynx 10. Although specific attachment means are described, it should be appreciated that any means for movably interconnecting the vocal folds 14 and 16 through a mechanical component as described herein are contemplated.

INDUSTRIAL APPLICABILITY

The present disclosure is generally applicable to devices for treating unilateral vocal fold paralysis. More specifically, the present disclosure is applicable to vocal fold movement translation devices including a reverse motion linkage configured to move a non-working vocal fold in a first movement direction in response to movement of a working vocal fold in a second movement direction that is opposite the first movement direction. Yet further, the present disclosure is applicable to a mechanical component for translating the movement of the working vocal fold into a reverse movement of the non-working vocal fold.

Referring now to FIGS. 1-8, the vocal folds 12 and 14 are housed within the larynx 10 and, in addition to performing other functions, are movable to produce sound. In particular, as air is moved past the vocal folds 12 and 14, as the vocal folds 12 and 14 are moved between abducted and adducted positions, the vocal folds 12 and 14 vibrate to produce sound. The vocal folds 12 and 14 are attached to and movable by a pair of arytenoid cartilages 16 and 18. If nerves going to one of the vocal folds 12 and 14 become damaged, the vocal fold 12 or 14 may become weak or paralyzed. A paralysis of only one of the vocal folds 12 and 14 is generally referred to as unilateral vocal fold paralysis and may be caused by a number of conditions. As a result of unilateral vocal fold paralysis, a patient may be unable to speak clearly or loudly and/or may run out of air easily.

A vocal fold movement translation device 20, 40, 82, or 120, as disclosed herein, may be useful for patients experiencing unilateral vocal fold paralysis. In particular, a non-working vocal fold 12 may be interconnected with a working vocal fold 14 using a reverse motion linkage 42 or 122 of the vocal fold movement translation device 20, 40, 82, or 120. The reverse motion linkage 42 or 122 may receive an indication of a movement of the working vocal fold 14 in a first movement direction and, in response, moves the non-working vocal fold 12 in a second movement direction that is opposite the first movement direction. Specifically, the reverse motion linkage 42 or 122 is movable between a first configuration corresponding to an abducted position of the vocal folds 12 and 14, as shown in FIG. 1, and an adducted position of the vocal folds 12 and 14, as shown in FIG. 2.

According to the exemplary embodiment of FIG. 3, the reverse motion linkage 42 may include a single linkage mechanism 56, which includes a first lever 44 configured for attachment to the first arytenoid cartilage 16 supporting the non-working vocal fold 12, and a second lever 46 configured for attachment to the second arytenoid cartilage 18 supporting the working vocal fold 14. The single linkage mechanism 56 may, for example, include a rack and pinion mechanism 58. In particular, the first lever 44 may include a first toothed rack portion 60 and the second lever 46 may include a second toothed rack portion 62. The first toothed rack portion 60 may be in mesh with a first pinion gear 64 of the rack and pinion mechanism 58, while the second toothed rack portion 62 may be in mesh with a second pinion gear 66 of the rack and pinion mechanism 58. According to the attachment arrangement described above, inward movement of a first corner 28 of the second arytenoid cartilage 18 causes inward movement of the second lever 46. In particular, the rack and pinion mechanism 58 translates the inward movement of the second lever 46 into an inward movement of the first lever 44.

According to the exemplary embodiment of FIG. 4, a single linkage mechanism 80 may include a center lever 84. A first end 90 of the center lever 84 may be movably attached to a first lever 92 at a first movable pivot axis 94, while a second end 96 of the center lever 84 may be movably attached to a second lever 98 at a second movable pivot axis 100. The center lever 84 may be attached to innermost ends 102 and 104 of the first and second levers 92 and 98, with outermost ends 106 and 108 of the first and second levers 92 and 98 being configured for attachment to the vocal folds 12 and 14, such as through the arytenoid cartilages 16 and 18, as described above. The single linkage mechanism 80 of FIG. 4 may effectively move the non-working vocal fold 12 in a first movement direction in response to movement of the working vocal fold 14 in a second movement direction that is opposite the first movement direction.

According to the exemplary embodiment of FIG. 5, the vocal fold movement translation device 120 may include a reverse motion linkage 122 having two linkage mechanisms 124 and 126. The reverse motion linkage 122 may include a first lever 128 having an outermost end 130 configured for attachment to the first arytenoid cartilage 16 supporting the non-working vocal fold 12, and a second lever 132 having an outermost end 134 configured for attachment to the second arytenoid cartilage 18 supporting the working vocal fold 14. Each of the two linkage mechanisms 124 and 126 may include a center lever 136, 138 supported on a housing 140 at a fixed pivot axis 142, 144. The first center lever 136 may be movably attached to the first lever 128 at a first movable pivot axis 146 and movably attached to the second lever 132 at a second movable pivot axis 148. The second center lever 138 may be movably attached to the first lever 128 at a third movable pivot axis 150 and movably attached to the second lever 132 at a fourth movable pivot axis 152. The reverse motion linkage 122 may be movable between a first configuration, as shown in FIG. 5, corresponding to an abducted position of the vocal folds 12 and 14 (FIG. 1), and a second configuration, as shown in FIG. 6, corresponding to an adducted position of the vocal folds 12 and 14 (FIG. 2).

The vocal fold movement translation device disclosed herein provides a mechanical means for translating movement of a working vocal fold into corresponding, or reverse, movement of a non-working, or paralyzed, vocal fold. According to some embodiments, only portions of the movement may be translated in order to reduce the force exerted by the working vocal fold. In contrast to conventional methods of maintaining a medialized position of the non-working vocal fold, the device of the present disclosure only initiates a medialized position of the non-working vocal fold when required, such as when the working vocal fold moves toward the midline. As such, when the working vocal fold is not being used, the non-working vocal fold is returned to an open position, rather than remaining toward the midline and unnecessarily obstructing the airway.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A vocal fold movement translation device, comprising:
a reverse motion linkage configured to interface with a first vocal fold and a second vocal fold, wherein the reverse motion linkage includes a mechanical component configured to move the first vocal fold in a first movement direction in response to movement of the second vocal fold in a second movement direction that is opposite the first movement direction;
wherein the reverse motion linkage is movable between a first configuration corresponding to an abducted position of the first and second vocal folds and a second configuration corresponding to an adducted position of the first and second vocal folds.

2. The vocal fold movement translation device of claim 1, wherein the reverse motion linkage includes a first lever configured for attachment to a first cartilage supporting the first vocal fold and a second lever configured for attachment to a second cartilage supporting the second vocal fold.

3. The vocal fold movement translation device of claim 2, wherein the reverse motion linkage includes a single linkage mechanism interconnecting the first and second levers.

4. The vocal fold movement translation device of claim 3, wherein the single linkage mechanism includes a rack and pinion mechanism.

5. The vocal fold movement translation device of claim 4, wherein the first lever includes a first toothed rack portion and the second lever includes a second toothed rack portion, wherein the first toothed rack portion is in mesh with a first pinion gear and the second toothed rack portion is in mesh with a second pinion gear.

6. The vocal fold movement translation device of claim 5, wherein the first vocal fold corresponds to a non-working vocal fold and the second vocal fold corresponds to a working vocal fold, wherein, during a rotation of the first and second pinion gears, a travel distance of the second lever is greater than a travel distance of the first lever.

7. The vocal fold movement translation device of claim 5, wherein the first and second pinion gears are supported on a housing at a common axis of rotation, wherein the housing is configured for attachment to a laryngeal wall.

8. The vocal fold movement translation device of claim 3, wherein the single linkage mechanism includes a center lever supported on a housing at a fixed pivot axis, wherein a first end of the center lever is movably attached to the first lever at a first movable pivot axis and a second end of the center lever is movably attached to the second lever at a second movable pivot axis.

9. The vocal fold movement translation device of claim 8, wherein the first vocal fold corresponds to a non-working vocal fold and the second vocal fold corresponds to a working vocal fold, wherein the fixed pivot axis is closer to the first movable pivot axis than the second movable pivot axis.

10. The vocal fold movement translation device of claim 8, wherein the housing is configured for attachment to a laryngeal wall.

11. The vocal fold movement translation device of claim 2, wherein the reverse motion linkage includes two linkage mechanisms.

12. The vocal fold movement translation device of claim 11, wherein each of the two linkage mechanisms includes a center lever supported on a housing at a fixed pivot axis, wherein the center lever is movably attached to the first lever at a first movable pivot axis and movably attached to the second lever at a second movable pivot axis.

13. The vocal fold movement translation device of claim 12, further including a spring mechanism configured to bias the reverse motion linkage toward the first configuration.

14. A method of operating a vocal fold movement translation device, comprising steps of:

interfacing with a non-working vocal fold and a working vocal fold using a reverse motion linkage of the vocal fold movement translation device;
receiving an indication of a movement of the working vocal fold in a first movement direction at the reverse motion linkage; and
moving the non-working vocal fold in a second movement direction using a mechanical component of the reverse motion linkage in response to the movement of the working vocal fold, wherein the second movement direction is opposite the first movement direction.

15. The method of claim 14, further including moving the reverse motion linkage between a first configuration corresponding to an abducted position of the non-working and working vocal folds and a second configuration corresponding to an adducted position of the non-working and working vocal folds.

16. The method of claim 15, further including:
attaching a first lever to a first cartilage supporting the non-working vocal fold and attaching a second lever to a second cartilage of the working vocal fold; and
interconnecting the first and second levers through a linkage mechanism.

17. The method of claim 16, further including translating a travel distance of the second lever into a travel distance of the first lever using a rack and pinion mechanism.

18. The method of claim 16, further including translating a travel distance of the second lever into a travel distance of the first lever using a center lever having a fixed pivot axis, wherein the center lever is movably attached to the first lever at a first movable pivot axis and movably attached to the second lever at a second movable pivot axis.

19. The method of claim 16, further including biasing the reverse motion linkage toward the first configuration.

20. The method of claim 16, further including attaching a housing of the linkage mechanism to a laryngeal wall.

\* \* \* \* \*